United States Patent [19]
Bach et al.

[11] Patent Number: 6,015,685
[45] Date of Patent: Jan. 18, 2000

[54] ANCROD PROTEINS, THEIR PREPARATION AND USE

[75] Inventors: Alfred Bach, Ladenburg; Karl-Hermann Strube, Speyer; Wolfgang Koerwer, Gruenstadt, all of Germany

[73] Assignee: BASF Aktiengesellschaft, Ludwigshafen, Germany

[21] Appl. No.: 07/690,957

[22] PCT Filed: Nov. 25, 1989

[86] PCT No.: PCT/EP89/01427

§ 371 Date: May 14, 1991

§ 102(e) Date: May 14, 1991

[87] PCT Pub. No.: WO90/06362

PCT Pub. Date: Jun. 14, 1990

[30] Foreign Application Priority Data

Dec. 10, 1988 [DE] Germany ............................ 38 41 736

[51] Int. Cl.$^7$ ............................ C12N 15/12; C07H 21/04
[52] U.S. Cl. ................. 435/69.1; 435/172.3; 435/252.3; 435/252.33; 435/254.2; 435/320.1; 435/325; 536/23.1; 536/23.5
[58] Field of Search ................. 435/69.1, 320.1, 435/240.2, 252.3, 252.33, 35, 172.3, 325, 254.2; 536/27, 23.1, 23.5; 424/98; 530/856

[56] References Cited

U.S. PATENT DOCUMENTS 3,879,369  4/1975  Nolan ........................................ 424/98
4,154,656  5/1979  Maurer ...................................... 424/98

FOREIGN PATENT DOCUMENTS 0 323 722  7/1989  European Pat. Off. .

OTHER PUBLICATIONS

Studies on the Coagulant Enzyme from *Agkistrodon Rhodostoma* Venom, Hatton, Biochem. J. (1973) 799–807, vol. 131.

Characterization of a Protein C Activator from *Agkistrodon Contortrix Contorix* Venom, Kisiel et al., The Journal of Biological Chemistry, vol. 262, No. 26, Sep. 15, 1987 12607–12613.

Primary Structure of a Protein C Activator from *Agkistrodon Contorix* . . . Biochemistry 1989, 28, 674–679, McMullen et al.

*Primary Examiner*—John L. LeGuyader
*Attorney, Agent, or Firm*—Keil & Weinkauf

[57] ABSTRACT

Pure glycosylated, partially glycosylated or unglycosylated polypeptides have the amino-acid sequence of ancrod, in which up to 5 amino acid residues can be replaced by residues of other natural amino acids, and are suitable for controlling diseases.

6 Claims, 11 Drawing Sheets

Figure 3:
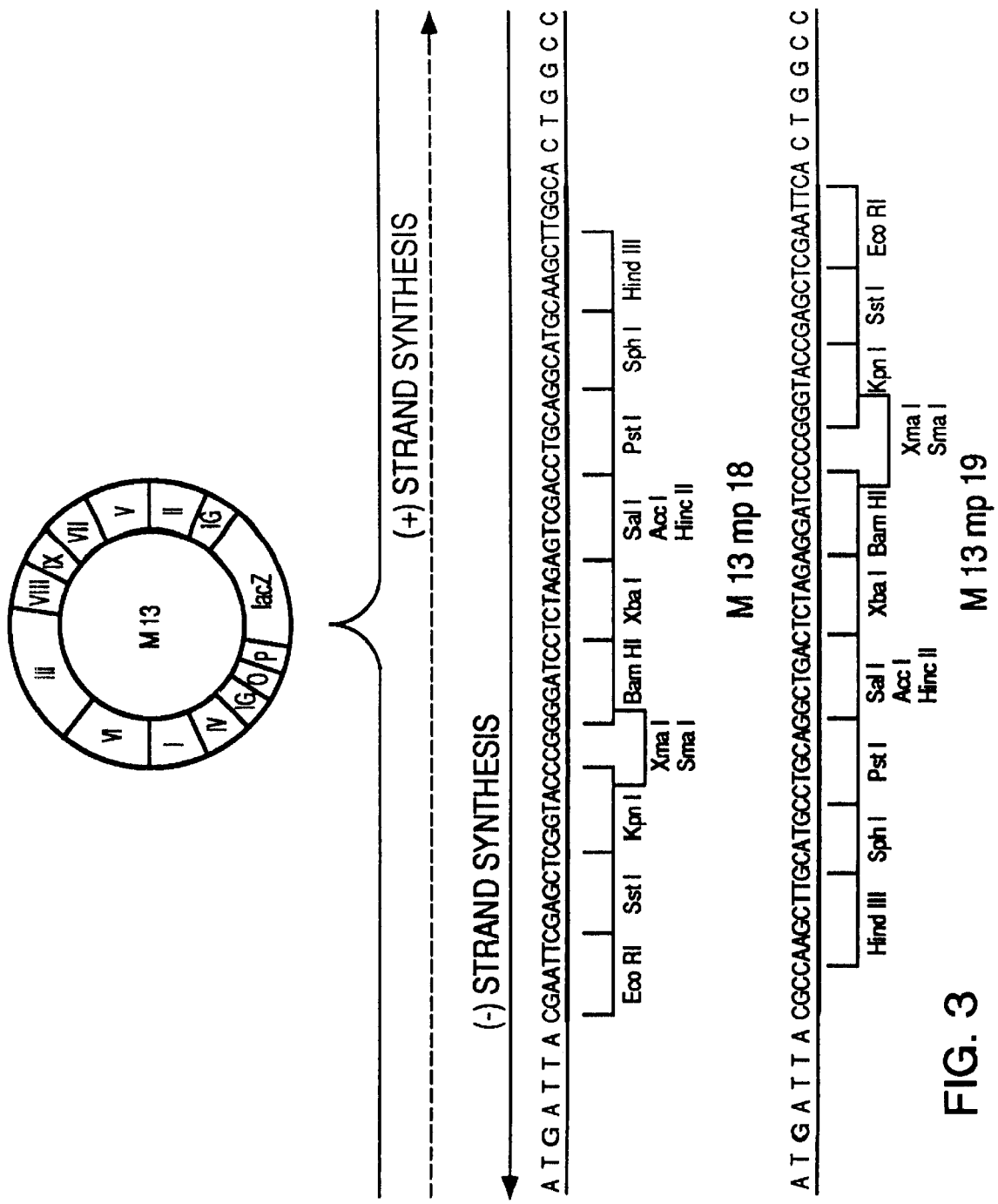
Figure 3B:
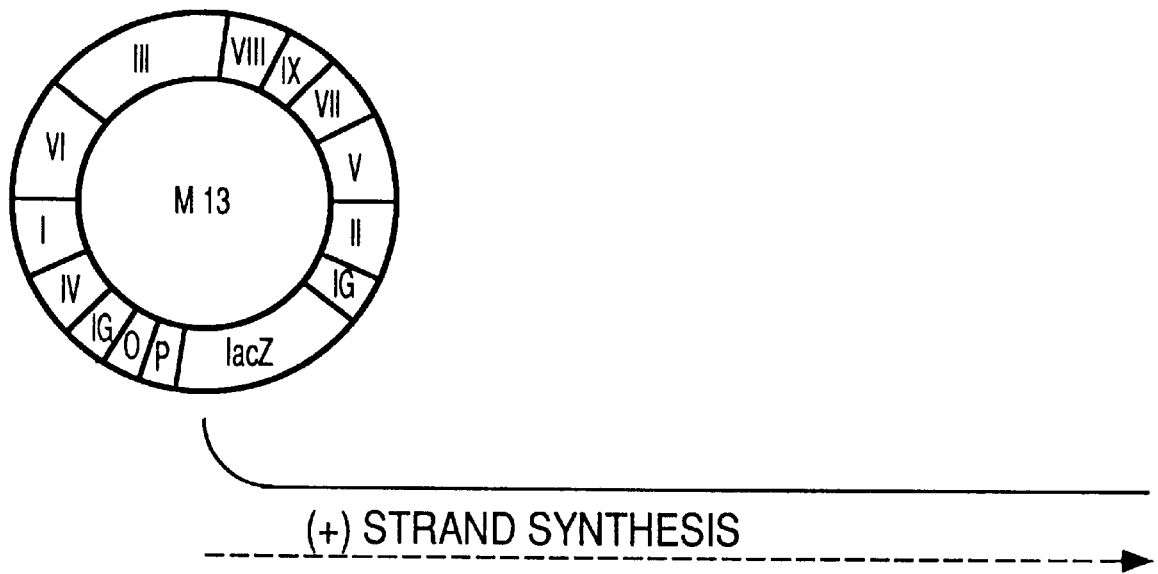

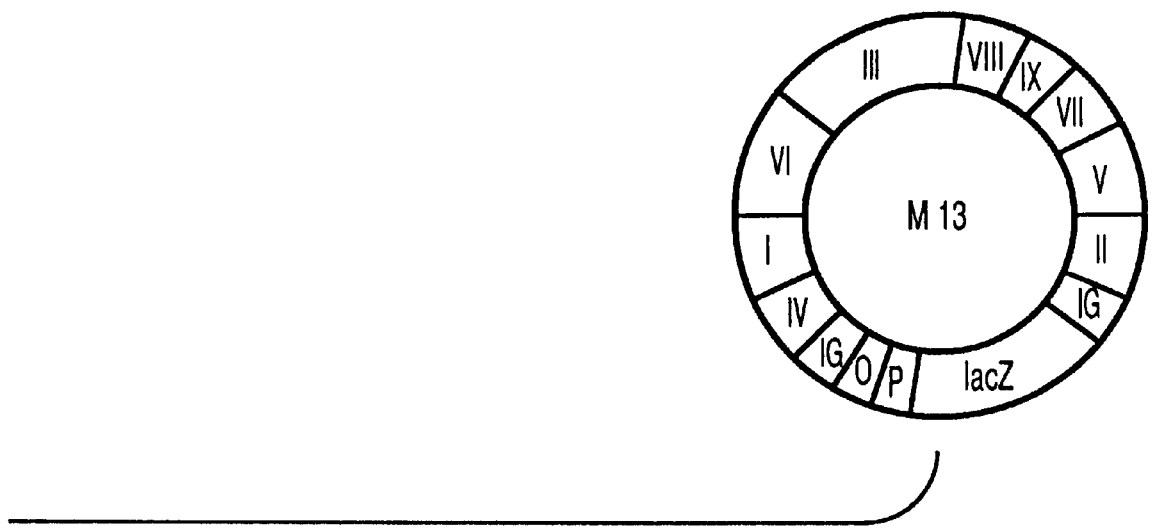
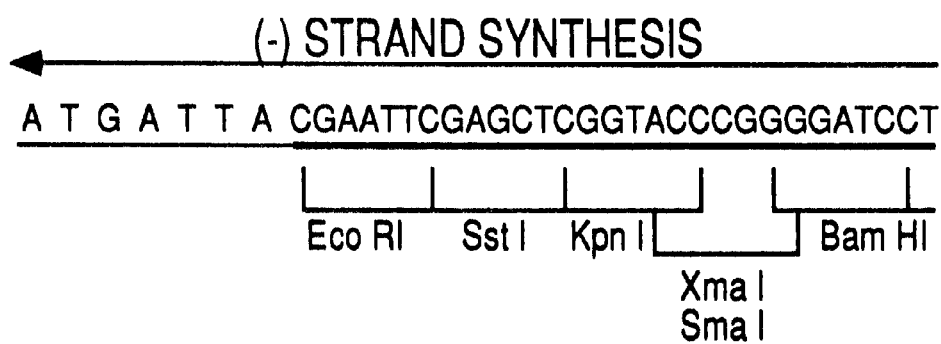
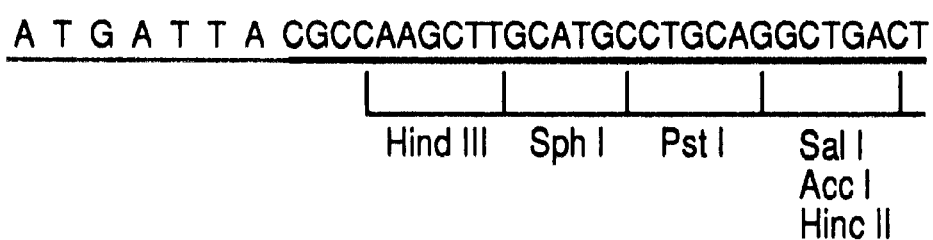
FIG. 3a

```
     CCATGGATGCATGCGGCAAAGAGCTTCTGC
  1 ---------+---------+---------+ 30
     GGTACCTACGTACGCCGTTTCTCGAAGACG
  c    M  D  A  C  G  K  E  L  L  R

GCAGAGTTGAAGCTATGATGCTGATCAGAG
 31 ---------+---------+---------+ 60
     CGTCTCAACTTCGATACTACGACTAGTCTC
  c    R  V  E  A  M  M  L  I  R  V -

TGCTAGCAAACCTTCTGATACTACAGCTTT
 61 ---------+---------+---------+ 90
     ACGATCGTTTGGAAGACTATGATGTCGAAA
  c    L  A  N  L  L  I  L  Q  L  S

CTTATGCACAAAAGTCTTCTGAACTGGTCA
 91 ---------+---------+---------+ 120
     GAATACGTGTTTTCAGAAGACTTGACCAGT
  c    Y  A  Q  K  S  S  E  L  V  I -

TTGGAGGTGATGAATGTAACATAAATGAAC
121 ---------+---------+---------+ 150
     AACCTCCACTACTTACATTGTATTTACTTG
  c    G  G  D  E  C  N  I  N  E  H

ATCGTTCCTTGTAGCCGTGTATGAAGGTA
151 ---------+---------+---------+ 180
     TAGCAAAGGAACATCGGCACATACTTCCAT
  c    R  F  L  V  A  V  Y  E  G  T -

CAAATTGGACTTTTATCTGCGFTGGGGTTT
181 ---------+---------+---------+ 210
     GTTTAACCTGAAAATAGACGCCACCCCAAA
  c    N  W  T  F  I  C  G  G  V  L

TGATCCACCCGGAATGGGTGATCACCGCTG
211 ---------+---------+---------+ 240
     ACTAGGTGGGCCTTACCCACTAGTGGCGAC
  c    I  H  P  E  W  V  I  T  A  E -

AACACTGTGCCAGGAGACGTATGAACCTAG
241 ---------+---------+---------+ 270
     TTGTGACACGGTCCTCTGCATACTTGGATC
  c    H  C  A  R  R  R  M  N  L  V

TCTTTGGTATGCATAGAAAAAGTGAAAAAT
271 ---------+---------+---------+ 300
     AGAAACCATACGTATCTTTTTCACTTTTTA
  c    F  G  M  H  R  K  S  E  K  F -
```

FIG. 4a

```
        TTGACGATGAGCAGGAAAGATACCCAAAGA
301 ---------+---------+---------+ 330
        AACTGCTACTCGTCCTTTCTATGGGTTTCT
    c   D D E Q E R Y P K K

AAAGGTACTTTATTCGCTGCAACAAAACCC
331 ---------+---------+---------+ 360
        TTTCCATGAAATAAGCGACGTTGTTTTGGG
    c   R Y F I R C N K T R-

GTACCAGTTGGGACGAGGACATCATGTTGA
361 ---------+---------+---------+ 390
        CATGGTCAACCCTGCTCCTGTAGTACAACT
    c   T S W D E D I M L I

TCAGGCTGAACAAACCTGTTaacaacagtg
391 ---------+---------+---------+ 420
        AGTCCGACTTGTTTGGACAAttgttgtcac
    c   R L N K P V N N S E- aacacatcgctcctctcagcttgccttcca
421 ---------+---------+---------+ 450
        ttgtgtagcgaggagagtcgaacggaaggt
    c   H I A P L S L P S N accctcccattgtgggctcagattgccgtg
451 ---------+---------+---------+ 480
        tgggagggtaacacccgagtctaacggcac
    c   P P I V G S D C R V- ttatgggatggggctcaatcaatcgacgta
481 ---------+---------+---------+ 510
        aataccctaccccgagttagttagctgcat
    c   M G W G S I N R R I tacacgttttgtccgatgaacctcgttgtg
511 ---------+---------+---------+ 540
        atgtgcaaaacaggctacttggagcaacac
    c   H V L S D E P R C A- ctaacattaacctgcacaatttcacgatgt
541 ---------+---------+---------+ 570
        gattgtaattggacgtgttaaagtgctaca
    c   N I N L H N F T M C gtcatggacttttcgaaagatgccgaaga
571 ---------+---------+---------+ 600
        cagtacctgaaaagctttctacggcttct
    c   H G L F R K M P K K-
```

FIG. 4b

```
              aaggcagagtattgtgtgcaggtgacctgc
      601 ---------+---------+---------+ 630
              ttccgtctcataacacacgtccactggacg
          c    G  R  V  L  C  A  G  D  L  R gaggacgcagagattcatgtaatagtgact
      631 ---------+---------+---------+ 660
              ctcctgcgtctctaagtacattatcactga
          c    G  R  R  D  S  C  N  S  D  S - ctgggggacctctcatttgtaatgaagaac
      661 ---------+---------+---------+ 690
              gacccccctggagagtaaacattacttcttg
          c    G  G  P  L  I  C  N  E  E  L tccatggcattgtagctaggggacccaatc
      691 ---------+---------+---------+ 720
              aggtaccgtaacatcgatcccctgggttag
          c    H  G  I  V  A  R  G  P  N  P - cttgtgcccagccgaataagcctgccctct
      721 ---------+---------+---------+ 750
              gaacacgggtcggcttattcggacgggaga
          c    C  A  Q  P  N  K  P  A  L  Y acaccagcgtctacgattatcgtgactggg
      751 ---------+---------+---------+ 780
              tgtggtcgcagatgctaatagcactgaccc
          c    T  S  V  Y  D  Y  R  D  W  V - tcaataatgttattgcaggaaatgcaactt
      781 ---------+---------+---------+ 810
              agttattacaataacgtcctttacgttgaa
          c    N  N  V  I  A  G  N  A  T  C gctctccataaaaatagttaagaggagaaa
      811 ---------+---------+---------+ 840
              cgagaggtattttatcaattctcctcttt
          c    S  P  *  K  *  L  R  G  E  N -
```

FIG. 4c

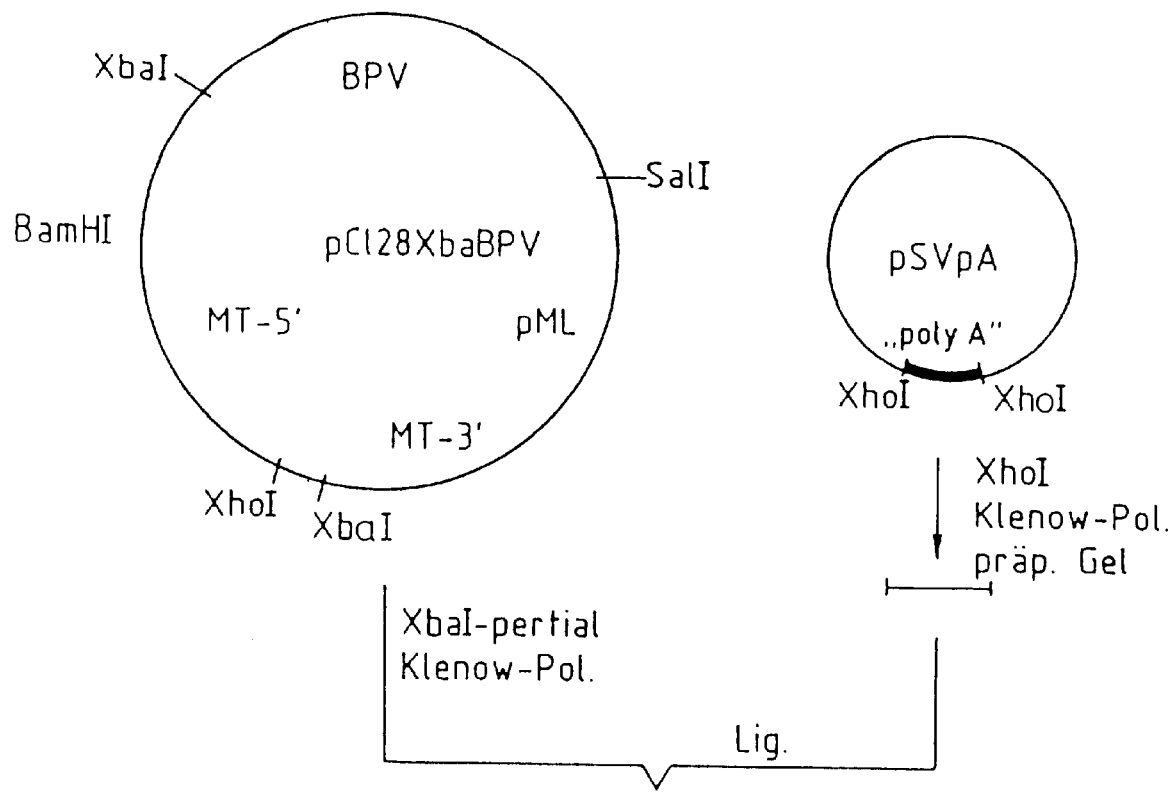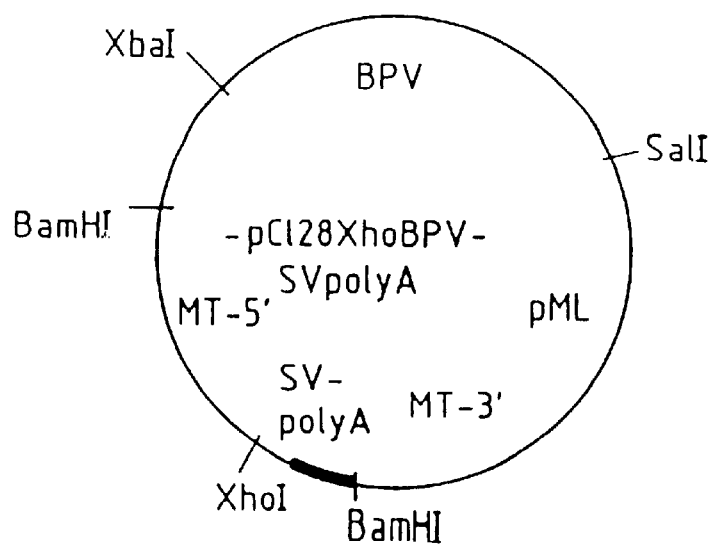
FIG. 6

ANCROD PROTEINS, THEIR PREPARATION AND USE

BACKGROUND OF THE INVENTION

The present invention relates to ancrod proteins, their preparation and use for the prophylaxis and therapy of diseases.

Ancrod is a fibrinogen-splitting enzyme which can be obtained from the venom of the Malayan pit viper (*Agkistrodon rhodostoma*) and has anticoagulant properties (Biochem, J. 131 (1973) 799).

Ancrod has a molecular weight of about 38,000 Dalton and a carbohydrate content of about 38%.

The process for preparing ancrod is elaborate. The extremely venomous Malayan pit viper must be raised in snake farms and milked by hand before the biochemical processing of the secretion for the isolation of ancrod can be started. Ancrod prepared in this way can be used for only a limited time because signs of resistance may appear after 6 to 8 weeks and are presumably due to the formation of ancrod-neutralizing antibodies. In isolated cases there are also hemorrhagic complications.

We have now found and prepared pure ancrod proteins which are superior, in terms of therapeutic use and the preparation, to the ancrod obtainable hitherto.

SUMMARY OF THE INVENTION

The present invention relates to pure glycosylated, partially glycosylated or unglycosylated polypeptides having the following aminoacid sequence:

```
1    VIGGDECNIN EHRFLVAVYE GTX¹WTFICGG VLIHPEWVIT AEHCARRRMN

51   LVFGMHRKSE KFDDEQERYP KKRYFIRCX²K TRTSWDEDIM LIRLNKPVX³N

101  SEHIAPLSLP SNPPIVGSDC RVMGWGSINR RIHVLSDEPR CANINLHX⁴FT

151  MCHGLFRKMP KKGRVLCAGD LRGRRDSCNS DSGGPLICNE ELHGIVARGP

201  NPCAQPNKPA LYTSVYDYRD WVNNVIAGX⁵A TCSP
``` where $X^1$, $X^2$, $X^3$, $X^4$ and $X^5$ are residues of natural α-aminoacids.

The individual letters therein denote the aminoacids (cf. Lubert Stryer, Biochemie, 1979, p. 12, S. R. Vieweg).

The amino-acid residues $X^1$, $X^2$, $X^3$, $X^4$ and $X^5$, which can be identical or different, represent N, Q, S, T, G, D, E, K, R, P, but preferably N, Q, S and T and, in particular, N and Q.

The present invention also relates to DNA sequences which code for the abovementioned proteins, as well as to vectors which contain these DNA sequences.

The proteins according to the invention can be prepared by known methods of genetic manipulation.

Thus, it is possible for mRNA to be isolated from the glandular tissue of a Malayan pit viper (*Agkistrodon rhodostoma*) and to be converted into double-stranded cDNA. After this cDNA has been inserted into a commercial cloning vector, for example λ gt 10, a cDNA library is set up. For the methods used for this, reference may be made, for example, to Maniatis et al., Molecular Cloning, CSH Press (1982). The screening of such gene banks with radiolabeled oligonucleotide probes is by now also a widely used and described method. It is possible by this process to isolate and characterize a cDNA clone which has homology with the oligonucleotide probe. This process is described in "DNA cloning Vol. I, IRL Press, 1985.

It is easy with the aid of restriction enzymes to obtain the cDNA characterized in this way. The fragments obtained thereby can be used, where appropriate in conjunction with chemically synthesized oligonucleotides, adaptors or gene fragments, to clone the sequences coding for the protein. The incorporation of the gene fragments or synthetic DNA sequences into cloning vectors, for example the commercial plasmids M13mp or pkk-223-3, is carried out in a conventional manner. It is also possible to provide the genes or gene fragments with suitable control regions which have been chemically synthesized or isolated from bacteria, phages, eukaryotic cells or viruses thereof and which make it possible for the proteins to be expressed.

The transformation or transfection of suitable host organisms with the hybrid plasmids obtained in this way is likewise known and described in detail (M. Wigler et al., Cell 16 (1979) 777–785; F. L. Graham and A. J. van der Eb, Virology 52 (1973) 456–467). It is also possible to provide the hybrid plasmids with appropriate signal sequences which allow the polypeptides to be secreted into the medium.

The vectors which can be used for expression in mammalian cells are those which place the gene which is to be expressed, in this case the "ancrod"-cDNA, under the control of the mouse metallothionein or the viral SV40 promoter (J. Page Martin, Gene, 37 (1985) 139–144). The presence of the methionine start codon and the leader/prosequence of the gene for the ancrod protein is necessary for expression. Clones which have copies of these vectors as episomes or integrated into the genome are then isolated. Particularly advantageous are the integration and expression of the foreign gene on the basis of the bovine papilloma virus. The construction of shuttle vectors is possible in conjunction with prokaryotic sequences which code for replication in bacterial cells and antibiotic resistance. The construction and multiplication of the plasmid takes place initially in bacterial cells; subsequently, transfer into eukaryotic cells, for example into the mouse fibroblast cell line c127, is carried out.

It is also possible to use other cell systems, for example yeast and other fungi, insect cells as well as animal and human cells such as, for example, CHO, COS, L and 293 cells, in conjunction with suitable expression vectors for the expression of the cloned cDNA.

These eukaryotic expression systems have the advantage that they are able to secrete their products efficiently and usually in the natural form. In addition, they are capable of post-translational modification of their products.

Thus, when ancrod protein is expressed in eukaryotic cells it acquires additional glycoside side-chains. These side-chains are not present in polypeptides prepared in bacteria. The glycoside side-chains can also be completely or partially removed enzymatically with the aid of appropriate glycosidases. Most of the eukaryotic proteins expressed in bacteria occur in the cell as denatured inclusion bodies and have to be renatured by protein chemical methods. In addition, bacteria are often unable to eliminate the initiator amino acid methionine from the completed protein.

It is possible by use of secretion systems to circumvent these difficulties (Donald Oliver, Ann. Rev. Microbiol. 39 (1985) 615–48; John Ghrayeb et al. The EMBO Journal 3, 1984, 2437–2442.

However, it is also possible, because of the degeneracy of the genetic code, to use other DNA sequences, for example chemically synthesized genes with different DNA sequences, for the expression of ancrod proteins. Variants of ancrod protein with a similar action can be prepared with the aid of the cloned gene.

DNAs coding for the variants are derived from the original cloned gene by mutation (insertion, deletion, point mutation, hybrid formation).

The resulting polypeptides are purified by separation from the culture medium using affinity and ion exchange chromatography or by hydrophobic chromatography using conventional processes.

The claimed polypeptides are obtained in pure form, that is to say free of hemorrhagic residues from the snake's venom gland secretion, with a purity of greater than 97%.

The present invention also relates to drugs which contain the ancrod protein prepared according to the invention, where appropriate in a pharmaceutically tolerated carrier or binder. The drugs can also contain combinations of the ancrod protein prepared according to the invention with other pharmacologically active therapeutics such as, for example, with thrombolytics (tPA, streptokinase), hirudin or thromboxane-receptor antagonists.

Further embodiments of the invention are described in detail in the examples.

Reference may be made for methods of genetic manipulation to, for example, the manual by Maniatis et al. "Molecular Cloning", Cold Spring Harbor Laboratory, 1982 or "DNA cloning" Vol. I–III IRI Press 1985–87 edited by D. M. Glover.

The polypeptides according to the invention are suitable for the treatment of glomerulonephritis, myocardial infarct, non-ischemic stroke, disturbances of peripheral arterial blood flow (especially atherosclerosis obliterans, thrombangitis obliterans, diabetic microangiopathy and Raynaud's disease), unstable angina pectoris, deep venous thrombosis and other thromboses, rethrombosis after thrombolytic therapy, rethrombosis after vascular surgery such as for arterial or venous angioplastic implants and for preventing thromboses in an extracorporeal circulation.

The pure polypeptides described herein do not give rise to the hemorrhages and thromboembolic complications hitherto observed after administration of ancrod isolated from snakes. Furthermore, the polypeptides, which differ in the sugar structure from the enzyme isolated from snake venom, have the advantage that they can be administered for considerably longer than the product obtained from snake venom without signs of resistance appearing.

The ancrod protein is used in the form of a physiologically tolerated solution. The solution expediently contains a preservative such as, for example, chlorobutanol. Ancrod protein is generally injected subcutaneously. Treatment can be on an inpatient basis or else, if regular checks of the fibrinogen concentration which are necessary for monitoring the therapy are ensured, an outpatient basis.

Intravenous administration of ancrod is possible but should be performed only in exceptional cases and with observation in hospital.

The dosage of ancrod protein must always be established for the individual. The crucial factor is the behavior of the plasma fibrinogen concentration. It must be reduced slowly to 70–100 mg/ml of plasma. The fibrinogen concentration must be adjusted to values within this range throughout the entire treatment period.

Under these conditions there is, inter alia, an adequate improvement in the flow properties of the blood, a reduction in the serum PAI-1 and $PGI_2$ concentrations and an increase in the serum tPA concentration.

EXAMPLE 1

Protein Chemical Analysis of Ancrod 1.0 Partial Determination of the Amino-Acid Sequence of Ancrod The starting point for the cloning of ancrod protein was the identification of amino-acid sequences in the commercial glycoprotein from *Agkistrodon rhodostroma*. The methods used for this were as follows: the disulfide bridges in the glycoprotein were initially reduced and subsequently carboxymethylated. A portion of the resulting carboxymethylated glycoprotein was fragmented with trypsin, and the resulting (glyco)peptides were fractionated by reversed phase (r)HPLC. The amino-acid sequence of individual protein fractions was then determined by gas phase sequence analysis. Another portion of the carboxymethylated ancrod was then used for determination of the N-terminal amino-acid sequence, likewise by gas phase sequence analysis.

1.1 Reduction and Carboxymethylation of Ancrod 3.5 ml (protein concentration 3.56 mg/ml) of ancrod (proprietary name ARWIN), dissolved in 0.1 M phosphate, 0.1 M NaCl, 0.3% trichloro-tertiary-butyl alcohol pH 6.7–7.0, were initially subjected to exhaustive dialysis against 50 mM ammonium acetate buffer pH 7.0. The protein solution in a different buffer obtained in this way was freeze-dried. The lyophilisate was dissolved in 6 ml of reduction buffer (6 M guanidine, 0.2 M tris/HCl, 1 mM EDTA, 130 mM DTT, 0.01% TWEEN 80, pH 8.6) and incubated at 37° C. overnight. The carboxymethylation was then started by addition of 300 mg of iodoacetamide. After incubation at 0° C. in the dark for 1 h, the reaction was stopped by addition of 300 µl of β-mercaptoethanol, and the sample was dialyzed exhaustively against water. The carboxymethylated protein obtained in this way was freeze-dried in 0.5 ml portions after 25 µl (corresponding to about 50 µg) had previously been removed for determination of the N-terminal sequence (1.2).

1.2 N-terminal Sequencing of Ancrod

The (glyco)protein solution obtained after reduction and carboxymethylation (25 µl, see 1.1) was evaporated to dryness. The (glyco)protein was taken up in 20 µl of formic acid and diluted with 10 µl of $H_2O$ and then pipetted onto a glass fiber filter coated with POLYBREN. Sequencing in a gas-phase sequenator (Applied Biosystems) was then started. The liberated amino acids were detected on-line after derivatization as PTH amino acids (phenylthiohydantoins) with PITC (phenyl isothiocyanate) and rHPLC fractionation. A detailed description of the procedure is to be found in the operating instructions for the gas-phase sequenator.

1.3 Fragmentation of Carboxymethylated Ancrod 4 mg of carboxymethylated ancrod were dissolved in 500 µl of 0.1 M tris/HCl, 1 M guanidine, pH 8.5, and 100 µl (200 µg) of trypsin solution (sequencing grade, Boehringer Mannheim) were added. After incubation at 37° C. for 16 h, the reaction was stopped by heating the mixture at 95° C. for 5 min. The sample was then stored at −20° C. until used further.

1.4 Fractionation of the Trypsinized Peptides

Figure 1:
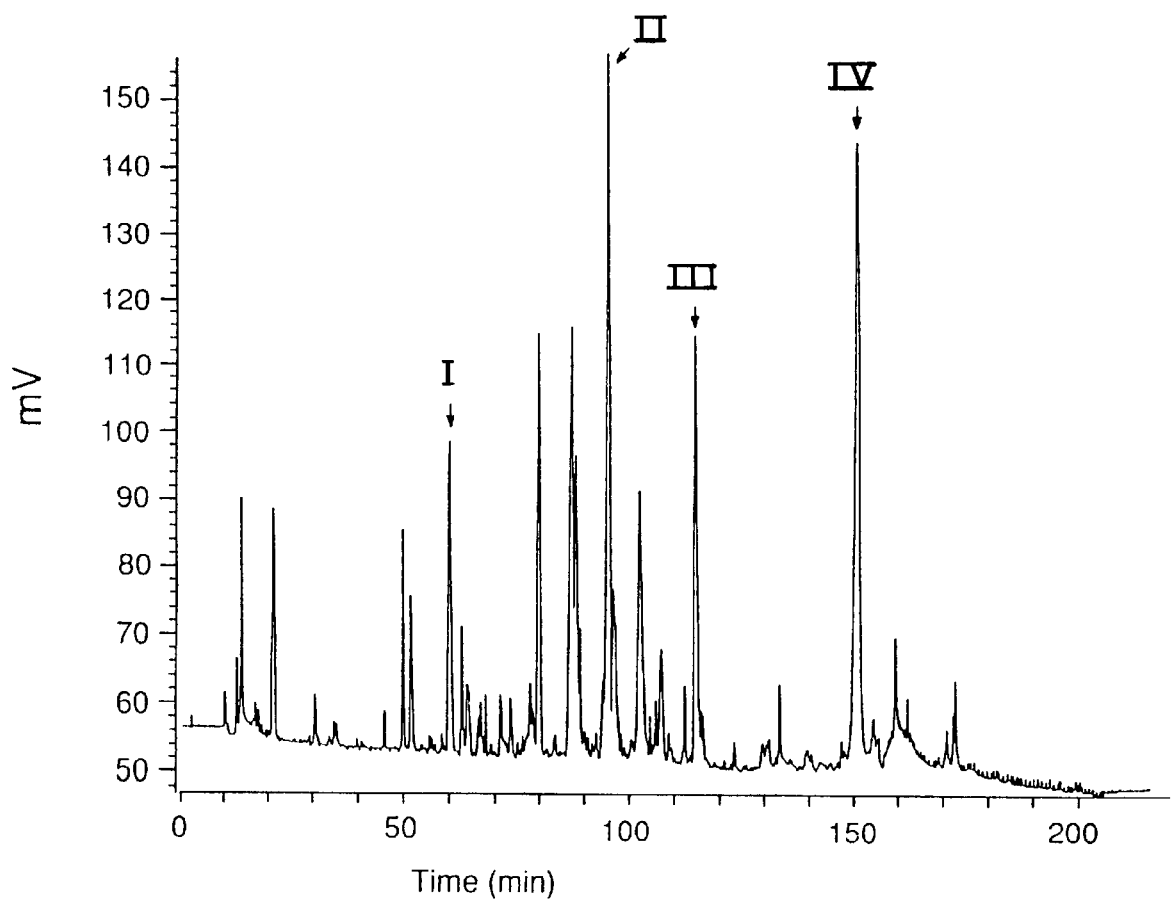

The (glyco)peptide mixture obtained after reduction, carboxymethylation and trypsin digestion was fractionated by rHPLC on a HP 1090 system (Hewlett Packard) using a VYDAK C-18 widepore column (Cat. No. 201TP54) in a TFA/acetonitrile gradient system. About 1.3 mg of protein, corresponding to 200 µl from 1.3, were applied to the column and eluted by applying a linear acetonitrile gradient (1–45% in 190 min). The progress of the chromatography was followed by measuring the UV absorption at 230 nm. The chromatogram obtained by this is shown in FIG. 1. The eluted peptides, identified by I–IV in FIG. 1, were evaporated to dryness in a concentrator. The gas-phase sequenator was used to establish the amino-acid sequences of the individual (glyco)peptides obtained in this way.

1.5 Identified Amino-Acid sequences a) N-terminal sequencing after reduction and carboxymethylation $V^1/_K$GGDECN$^1/_K$NEHRFLVAVYEGT-WT b) Amino acid sequencing after rHPLC (for identification of the fractions, see FIG. 1)

I YFI/K

II GPNPEAQPNKPALYTSIYDY

III TSWDEDIMLIR

IV FLVAVYEGT-WTFIEGGVLIHPEWVITAEH

EXAMPLE 2

Isolation of a cDNA Clone for Ancrod from the Malayan Pit Viper (*Agkistrodon rhodostoma*)

1 g of venom gland tissue from a 5-year old snake of the genus [sic] *Agkistrodon rhodostoma* was dissolved in 6 M guanidinium thiocyanate, 5 mM sodium citrate (pH 7.0), 0.1 M 2-mercaptoethanol, 0.5% sarcosyl in an ULTRA-TURAX. Coarse cell debris was removed by centrifugation at 3000 rpm. The RNA was removed by centrifugation through a 5.7 M CsCl cushion at 45,000 rpm overnight. The polyA$^+$-contained [sic] RNA fraction was then removed by affinity chromatography on oligo(dT)-cellulose.

Figure 2A:
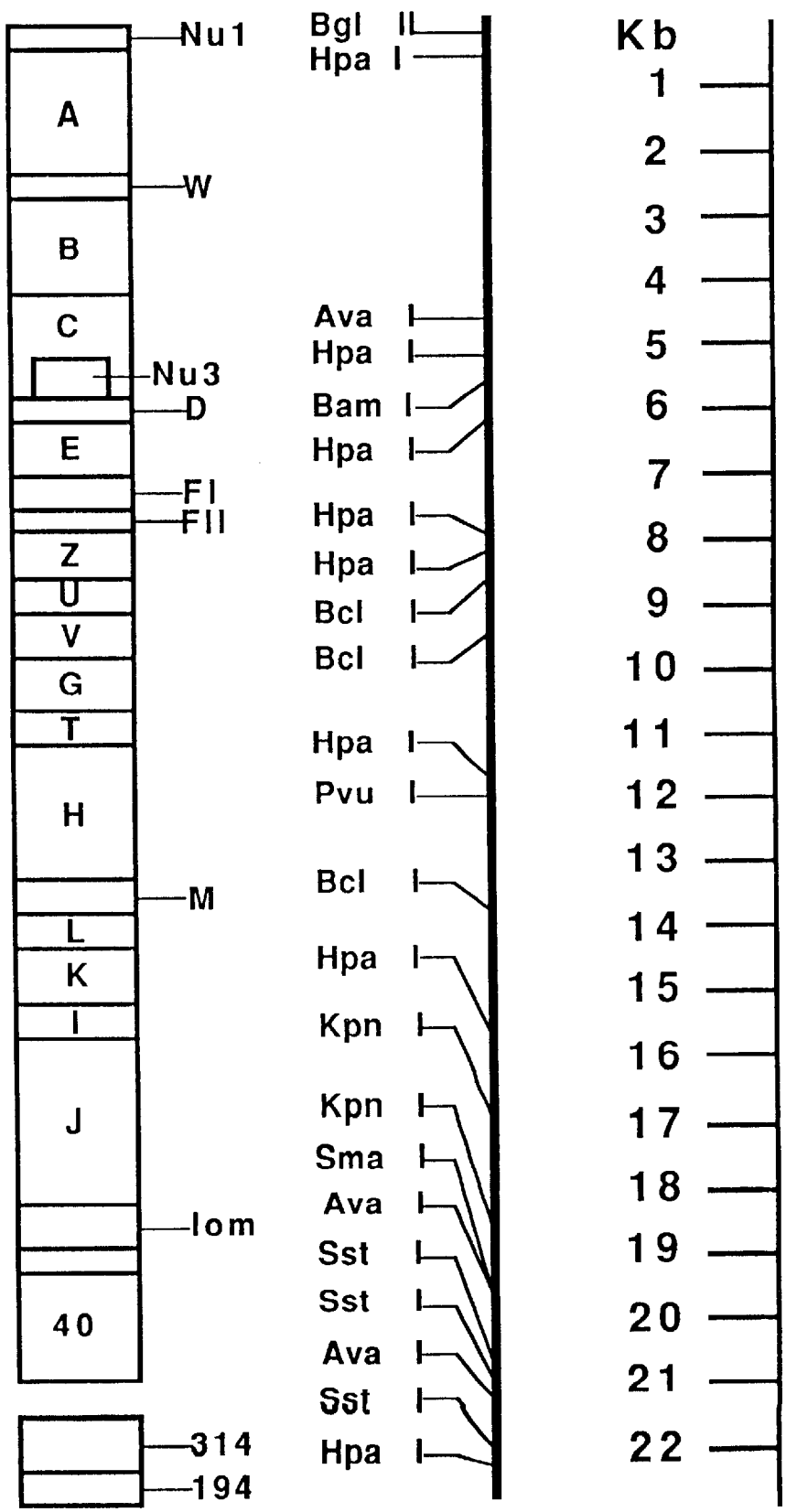
Figure 2B:
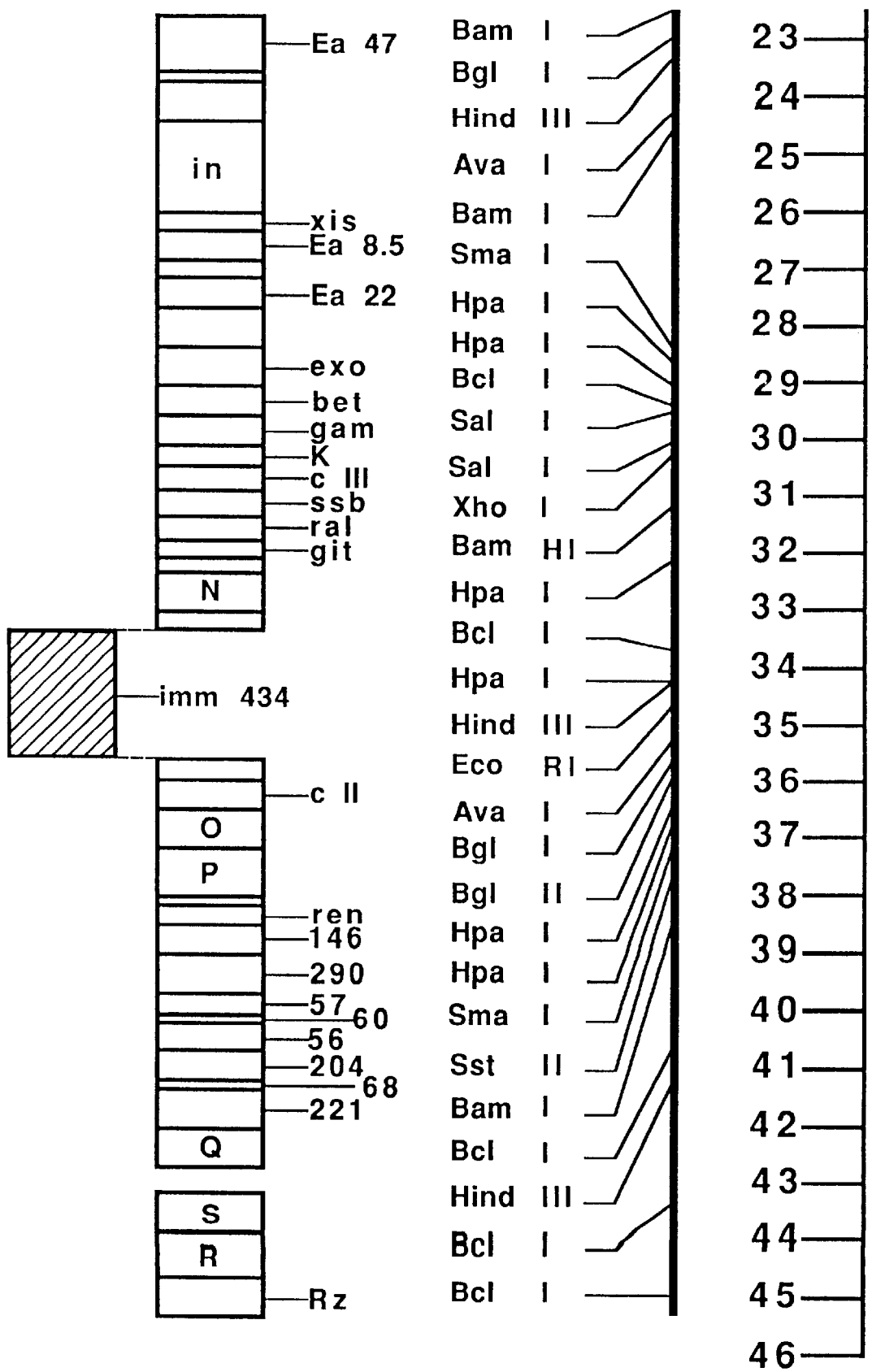

The polyA$^+$ RNA was transcribed into single-stranded cDNA with the aid of the enzyme AMV reverse transcriptase and oligo(dT)12–18 as starter. The second strand was synthesized using *E. coli* DNA polymerase I. An EcoRI adaptor with the sequence 5'AATT CCATGG ATG CATGC 3' was attached to the double-stranded cDNA with the aid of the enzyme T4-DNA ligase. The commercial phage vector λ gt 10 (FIG. 2) was linearized with the restriction enzyme EcoRI. The two DNAs were ligated together and packaged, using the commercial packaging extract, to give infectious phages. The recombinant phages were plated out with *E. coli* C 600 Hfl on NZYDT plates and incubated at 37° C. overnight. The cDNA library obtained in this way contained 2×10$^6$ independent clones. After the cDNA library had been amplified by conventional methods, 500,000 phages were plated out with C 600 Hfl cells. The phages were transferred to nitrocellulose filters, lysed with 0.5 N NaOH/1.5 M NaCl, and the denatured DNA was firmly bound to the filter by baking at 80° C. for 2 hours. The filters had been prehybridized in 6×SET buffer (1×SET=0.15 M NaCl, 15 mM tris/HCl, pH 7.4, 1 mM EDTA), 0.1% SDS and 5×Denhardt's solution (100×Denhardt=1 g of Ficoll, 1 g of polyvinylpyrrolidone, 1 g of BSA per 50 ml) at 68° C. for 4 h. An oligonucleotide probe, ARNT, which comprises 59 bases was prepared using a DNA synthesizer. It has the following sequence:

5' TGG ACT TTT ATT GAG GGC GGC GTG TTG ATT CAC CCG GAG TGG GTG ATT ACC GCC GAG CA 3'

This probe was labeled at the 5' end with γ-$^{32}$PATP. It was then incubated with the prehybridized filters in a solution which contained 6×SET, 0.1% SDS, 30% formamide, 5×Denhardt's and 10% dextran sulfate at 42° C. overnight, shaking gently. The filters were then washed several times in 6×SET/0.1% SDS at 42° C., dried and exposed to an X-ray film. Clones which gave a radioactive response in the screening were isolated and cultured further. One clone, called AR4 hereinafter, contained an approximately 0.9 kb insert which contains the coding region as well as 5'- and 3'-non-coding regions. Phage DNA from AR4 was prepared by incubation of the purified phages with protenase [sic] K (ad 60 µg/ml) at 55° C. for 1 h and subsequent phenol/chloroform extraction. Addition of 3 volumes of ethanol (−20° C.) precipitated the phage DNA, and it was transferred with a sterile injection needle into 70% strength ethanol, washed and briefly sedimented. The pellet was briefly dried in air and then suspended in TE buffer.

EXAMPLE 3

Preparation of Single-Stranded DNA which Codes for Ancrod

The starting point was the phage clone AR4 described in Example 2. It was cut preparatively with the restriction enzyme Eco RI. The Eco RI fragment which contained the ancrod-encoding DNA sequence was eluted from the gel by electrophoresis. 30 ng of this fragment were ligated at 4° C. for 12 h with 100 ng of the commercial cloning vector M13mp18 or M13mp19 (FIG. 3) which had been cut with EcoRI. The volume of the ligation mixture was 10 µl. The ligation was stopped by heating at 80° C. for 5 min.

1/10 of the volume of this ligation mixture was employed for the transformation of 100 µl of competent SR 101 cells. After transformation was complete, 60 µl of 0.2 M IPTG solution and 120 µl of XGal (20 mg/ml) were added to the transformation mixture. The mixture was plated out in NZYDT top agar on NZYDT agar plates with 200 µl of SR 101 cells (OD$_{600}$=1). The medium NZYDT is commercially available (GIBCO-BRL). Clones which contained the ancrod cDNA were identifiable by the absence of a blue coloration of the plaques. They were called mpAR4. The DNA sequence of the ancrod coding cDNA was elucidated by DNA sequence analysis (Sanger et al., Proc. Natl. Acad. Sci. U.S.A. 74 (1977) 5463–67) (FIG. 4).

4.1 Construction of Vectors for the Expression of Ancrod in Eukaryotic Cells

Figure 5:
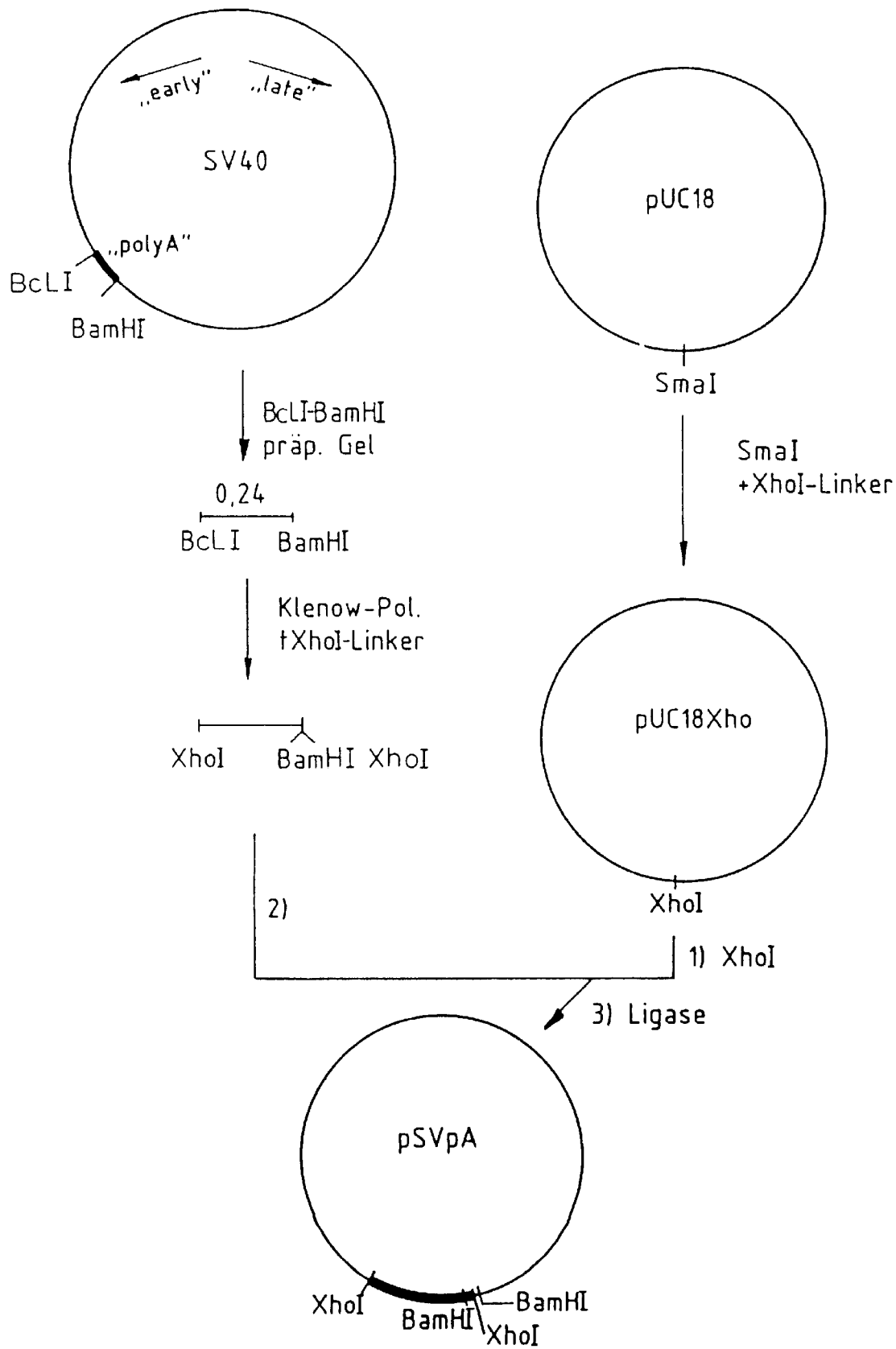

DNA of the monkey virus SV40 was cut with the restriction enzymes BamHI and BclI, and the 0.24 kb fragment was prepared by gel electrophoresis (FIG. 5). The ends were filled in with Klenow fragment in the presence of the four deoxynucleotide phosphates dATP, dCTP, dGTP and dTTP. XhoI linkers were subsequently ligated on.

In parallel, the commercial vector puC18 was linearized with the enzyme SmaI. XhoI linkers were then attached likewise. DNA from this vector ("pUC18Xho") was linearized with XhoI, treated with alkaline phosphatase and ligated with the 0.24 kb XholI [sic] SV40 fragment (see above). The result was pSVpA.

pSVpA DNA was cleaved preparatively with XhoI and incubated as above with Klenow polymerase in the presence of the four dNTPs. The 0.24 kb fragment was isolated on a gel.

At the same time, the eukaryotic expression vector CL28XhoBPV, produced by ligation of CL28x and pB2-2 (method of Reddy et al. DNA 6 (1987), 461–72), was partially cut with the restriction enzyme XbaI, ie. the incubation was limited in time such that the resulting molecules were cleaved at only one of the two XbaI recognition sequences, that is to say were linearized (FIG. 6). The mixture was then reacted with Klenow polymerase and dNTPs as described. The linear molecules were subsequently isolated by gel electrophoresis.

The linear pCL28XhoBPV fragments were then ligated with the pretreated 0.24 kb fragment from SV40. Transformation and screening of minilysates resulted in isolation of a clone which harbored the SV40 fragment in the former XbaI site located about 0.15 kB in the 3' direction from the XhoI site; this DNA ("pCL28XhoBPV-SVpoly-A") carried the SV40 transcription stop signal of the "early" genes.

Plasmid DNA from pCL28XhoBPV-SVpolyA was linearized with the restriction enzyme XhoI and treated with alkaline phosphatase. At the same time, mpAR4 was cleaved with the restriction enzyme Eco RI and attached to the 0.9 Kb fragment Xho linker using T4 ligase. The two fragments were connected together using T4 ligase. Transformation and analysis of minilysates resulted in isolation of a clone which contains the ancrod DNA singly and in the correct orientation: pCL28BPV-ancrod.

EXAMPLE 5
Transfection and Establishment of Cell Lines c127I cells (J. Virol. 26 (1978) 292; ATCC catalog of cell lines and hybridomas 5th edition 1985, p142) were transfected with BPV expression plasmids using the calcium phosphate coprecipitation method (Virology 52 (1973) 456; DNA cloning, Volume II, ed. D. M. Glover, IRL Press (1985) pages 143 et seq. and 213).

$5 \times 10^5$ C127I cells were inoculated into DMEM (Dulbeccos's modified eagles medium)+10% FCS (fetal calf serum) in 60 mm Petri dishes. The next day the medium was changed to MEM (modified eagles medium) containing 25 nM Hepes+10% FCS. A Ca phosphate co-precipitate was formed with $10^5$ g [sic] of CsCl-purified plasmid DNA and was cautiously placed on the C127I cells. The cells were incubated at 37° C., 7% $CO_2$ for 4 h. The efficiency of transfection was considerably increased by a subsequent glycerol shock treatment. For this, the medium was aspirated off the cells 4 h after the precipitate had been placed on them. The cells were incubated with 2 ml in each case of 15% glycerol/HBS (DNA cloning Vol. II, page 152) in a 60 mm Petri dish at room temperature for 3 min. The glycerol/HBS solution was aspirated off, and the cell lawn was washed with 3 ml of DMEM+10% FCS. The cells were incubated with DMEM+10% FCS at 37° C. and 7% $CO_2$. The DMEM+10% FCS was aspirated off and replaced by fresh medium three times a week. After 2–3 weeks, transfected cells which contain the BPV genome were evident as collections of transformed cells, called foci.

After the described foci had been subcloned the medium supernatants of the individual subclones were investigated for fibrinogen-splitting activity by conventional methods.

For production, the cell lines which had reached confluence were maintained in serum-free DMEM medium [sic]. Ancrod protein can be purified from the serum-free cell culture supernatant obtained in this way by conventional methods of protein chemistry and used for pharmacological and protein chemical analyses.

EXAMPLE 6
Production of Ancrod Protein in Bacteria
6.1 mpAR4 Mutation 2 pmol of the single-stranded mpAR4 were reacted with 5 pmol of an oligonucleotide with the sequence 5' CTC CAA TGA CCA TGG CAG AAG ACT TTT 3' which, apart from 3 base exchanges, was complementary with the region of mpAR4 DNA to be modified. The oligonucleotide had previously been phosphorylated with $T_4$ polynucleotide kinase. The mutation mixture had the following composition:

| | |
|---|---|
| single-stranded mpAR 4 | 1 μl (2 pmol) |
| kinased oligonucletide [sic] (including ATP from kinase reaction) | 1 μl (5 pmol) |
| 10 × ligase buffer | 5 μl |
| 1 mM dNTPs | 2.5 μl |
| 1 mM ATP | 4 μl |
| $H_2O$ | 36.5 μl |

The mutation mixture was incubated at 37° C. for 15 min, then cooled to room temperature and finally mixed with 1 unit of Klenow fragment (Boehringer Mannheim). After incubation at room temperature for 1 h, 200 units of $T_4$ ligase (Biolabs) were added. The mixture was then incubated at 4° C. for 16 h. Subsequently 5 μl of this mixture was used to transform component [sic] SR 101 cells. The phage plaques resulting from this were transferred to nitrocellulose. The filters were then washed in 5×SSC for 5 min, dried in air and baked at 80° C. for 2 h. Prehybridization and hybridization were carried out as described in Example 2. The filters were washed with 6×SET/0.1% SDS at 55–65° C. The oligonucleotide employed in the mutation mixture was used for hybridization. Positive clones were visualized by autoradiography. Positive clones differed from the mpAR4 sequence in 3 positions. This substitution results in an additional recognition site for the restriction enzyme NcoI being present in the mpAR4 DNA. This makes it possible to cleave this DNA in front of the codon (GTC) for the first amino acid (valine) of mature ancrod. The DNA obtained in this way was called mpAR4.1.

6.2 Subcloning in pKK 233-2 and Expression in Bacteria

A fragment which has a length of about 720 base-pairs was liberated from the double-stranded mpAR4.1 DNa by limited restriction with NcoI. The fragment contains the entire coding region for the mature ancrod protein. The 5' region of the coding strand of this is as follows:

5' C ATG GTC ATT GGA. . . .

This NcoI fragment was ligated with the commercial prokaryotic expression vector pKK233-2 (CLONETECH Cat. 6003-1) which had likewise been cut with NcoI. The ligation mixture was used to transform E. coli JM 105 cells. Clones which contained the recombinant plasmid were identified by the colony hybridization method which has been described many times. The oligonucleotide ARNT described in Example 2 was used as hybridization probe for this. The hybridization and washing conditions also corresponded to those described in Example 2. Clones which hybridized with the probe were characterized by restriction analysis in order to determine the orientation of the integrated fragment. Clones which contained the fragment in the orientation suitable for expression were cultivated in the appropriate medium. At an $OD_{660}$ of 1, IPTG was added to a final concentration of 10 mM. After further incubation at 37° C. for 4 h, the cells were harvested and the polypeptide was purified and renatured by standard processes.

EXAMPLE 7
Preparation of Carbohydrate-Free Ancrod Protein and Partially Carbohydrate-Free Ancrod Proteins in Mammalian Cells
7.0 Mutation of the Single-Stranded DNA The plasmid mpAR4 was mutated in such a way that one, some or all of the codon combinations for the tripeptide NXT or NXS were replaced by a codon combination for the tripeptide QXT or QXS respectively. The single-stranded DNA was mutated as in Example 6.1.

7.1 Single-Stranded DNA of the Clone mpAR4 was Mutated with the Nucleotide KH1

KH1: 5' AAAAGTCCACTGTGTACCTTCAT 3'

The mutated clones were identified by plaque hybridization with the probe KH1. Hybridization was carried out at 37° C. in 20% FA (formamide) and 4×SSC for 16 h. Washing was carried out in 5×SSC/0.1 [lacuna] SDS at 60° C. The resulting clones were called mpAR4.KH1.

7.2 Single-Stranded DNA of the Clone mp AR4.KH1 was Mutated with the Oligonucleotide $KH_2$

KH2: 5 TAC GGGTTTTCTGGCAGCGAATAAA 3'

The mutated clones were identified by plaque hybridization with the probe KH2. Hybridization was carried out at 37° C. in 20% FA and 5×SSC for 16 h, washing in 5×SSC/0.1% SDS at 65° C. The resulting clones were called mpAr4.KH1.2.

7.3 Single-Stranded DNA of the Clone mpAR4.KH1,2 was Mutated with the Oligonucleotide KH3

KH3: GTTCACTGTTCTGAACAGGTTTG 3'

The mutated clones were identified by plaque hybridization with the probe KH3. Hybridization was carried out at 35° C. in 5×SSC for 16 h, washing in 5×SSC/0.1% SDS at 58° C. The resulting clones were called mpAR4.KH 1,2,3.

7.4 Single-Stranded DNA of the Clone mpAR44.KH1,2,3 [sic] was Mutated with the Oligonucletide [sic] KH4

KH4: 5' ACATCGTGAACTGGTGCAGGTTAA

The mutated clones were identified by plaque hybridization with the probe KH4. Hybridization was carried out at 37° C. in 20% FA and 5×SSC for 16 h, washing in 5×SSC/0.1% SDS at 60° C. The resulting clones were called mpAR4.KH 1,2,3,4.

7.5 Single-Stranded DNA of the Clone mpAR4.KH1,2,3,4 was Mutated with the Oligonucletide [sic] KH5

KH5: 5' AGCAAGTTGCCTGTCCTGCAATAA 3'

The mutated clones were identified by plaque hybridization with the probe KH5. Hybridization was carried out at 37° C. in 20% FA and 5×SSC for 16 h, was in 5×SSC/0.1% SDS at 60° C. The resulting clones were called mpAR4.KH 1,2,3,4,5.

The ECORI [sic] inserts of the clones described in Examples 6.1–6.5 [sic] were recloned as described in Example 3 in a suitable eukaryotic expression vector and, after transfection (Example 4), expressed in the appropriate cells. The protein was purified from the cell culture supernatant by standard methods.

We claim:

1. A purified glycosylated, partially glycosylated or unglycosylated polypeptides having the following amino-acid sequence:

```
1    VIGGDECNIN EHRFLVAVYE GTX¹WTFICGG VLIHPEWVIT

AEHCARRRMN

51   LVFGMHRKSE KFDDEQERYP KKRYFIRCX²K TRTSWDEDIM

LIRLNKPVX³N

101  SEHIAPLSLP SNPPIVGSDC RVMGWGSINR RIHVLSDEPR

CANINLHX⁴FT

151  MCHGLFRKMP KKGRVLCAGD LRGRRDSCNS DSGGPLICNE

ELHGIVARGP

201  NPCAQPNKPA LYTSVYDYRD WVNNVIAGX⁵A TCSP,
``` where $X^1$, $X^2$, $X^3$, $X^4$ and $X^5$ are residues of natural α-amino acids.

2. A recombinant vector which contains a DNA sequence which codes for the polypeptide as claimed in claim 1.

3. The recombinant vector as claimed in claim 2, which is connected to an expression control sequence which makes expression possible in suitable host systems.

4. The recombinant vector as claimed in claim 3, wherein the expression control sequence is a promoter system effective in *E. coli*, a promoter system of an *E. coli* bacteriophage, a yeast expression control sequence or another eukaryotic expression control sequence.

5. A host organism which is a bacterium, a fungus, a human or other animal cell and which contains at least one recombinant vector as claimed in claim 2.

6. A process of genetic manipulation for the preparation of the polypeptides as claimed in claim 1, which comprises multiplying a host organism as claimed in claim 5 and isolating the polypeptides from the mixture by chromatography.

* * * * *